(12) United States Patent
Sterling et al.

(10) Patent No.: US 7,184,809 B1
(45) Date of Patent: Feb. 27, 2007

(54) PULSE AMPLITUDE INDEXING METHOD AND APPARATUS (75) Inventors: Bernhard B. Sterling, Danville, CA (US); Alexander K. Mills, San Antonio, CA (US)

(73) Assignee: Woolsthorpe Technologies, LLC, Brentwood, TN (US)

( * ) Notice: Subject to any disclaimer, the term of this patent is extended or adjusted under 35 U.S.C. 154(b) by 0 days.

(21) Appl. No.: 11/270,240

(22) Filed: Nov. 8, 2005

(51) Int. Cl.
*A61B 5/00* (2006.01)

(52) U.S. Cl. ............... 600/331; 600/322; 600/323

(58) Field of Classification Search .......... 600/309, 600/310, 322, 323, 331
See application file for complete search history.

(56) References Cited

U.S. PATENT DOCUMENTS

| | | | |
|---|---|---|---|
| 3,704,706 A * | 12/1972 | Herczfeld et al. | 600/324 |
| 3,734,086 A * | 5/1973 | Phelps, Sr. | 600/500 |
| 4,407,290 A * | 10/1983 | Wilber | 600/330 |
| 4,934,372 A | 6/1990 | Corenman et al. | |
| 5,193,543 A * | 3/1993 | Yelderman | 600/310 |
| 5,448,991 A * | 9/1995 | Polson et al. | 600/330 |
| 5,490,505 A | 2/1996 | Diab et al. | |
| 6,036,642 A | 3/2000 | Diab et al. | |
| 6,157,850 A | 12/2000 | Diab et al. | |
| 6,206,830 B1 | 3/2001 | Diab et al. | |
| 6,263,222 B1 | 7/2001 | Diab et al. | |
| 6,421,549 B1 * | 7/2002 | Jacques | 600/331 |
| 6,480,729 B2 * | 11/2002 | Stone | 600/323 |
| 6,537,225 B1 * | 3/2003 | Mills | 600/481 |
| 6,594,511 B2 * | 7/2003 | Stone et al. | 600/324 |
| 6,711,425 B1 * | 3/2004 | Reuss | 600/331 |
| RE38,492 E | 4/2004 | Diab et al. | |
| 6,719,705 B2 * | 4/2004 | Mills | 600/526 |
| 6,819,950 B2 * | 11/2004 | Mills | 600/322 |
| 6,921,367 B2 * | 7/2005 | Mills | 600/481 |
| 2004/0068164 A1 | 4/2004 | Diab et al. | |
| 2005/0177046 A1 * | 8/2005 | Mills | 600/481 |

* cited by examiner

*Primary Examiner*—Eric Winakur
*Assistant Examiner*—Etsub Berhanu
(74) *Attorney, Agent, or Firm*—Francis Law Group (57) ABSTRACT

The invention is method and apparatus for determining a physiological characteristic by detecting the intensity of light following tissue absorption at two wavelengths, estimating the pulse amplitude and indexing a calculated physiological characteristic to the estimated pulse amplitude. In one embodiment, the ratio of logarithms of absorbance signal amplitude is indexed to the pulse amplitude to improve the accuracy of arterial oxygen saturation as determined by a pulse oximeter.

28 Claims, 6 Drawing Sheets

PULSE AMPLITUDE INDEXING METHOD AND APPARATUS

FIELD OF THE PRESENT INVENTION

The present invention relates to the field of pulse oximetry. More specifically, the invention relates to a method and apparatus for improving the accuracy of pulse oximetry monitoring.

BACKGROUND OF THE INVENTION

Pulse oximetry provides critical information regarding the cardiorespiratory function of a patient. Oximeters continually monitor blood flow characteristics including, but not limited, to blood oxygen saturation of hemoglobin in arterial blood, the volume of individual blood pulsations supplying the flesh and the rate of blood pulsations corresponding to each heartbeat of the patient. Illustrative are the apparatus described in U.S. Pat. Nos. 5,193,543; 5,448,991; 4,407,290; and 3,704,706.

As is well known in the art, a pulse oximeter passes light through human or animal body tissue where blood perfuses the tissue, such as a finger, an ear, the nasal septum or the scalp, and photoelectrically senses the absorption of light in the tissue. The amount of light absorbed is then used to calculate the amount of oxyhemoglobin and estimate arterial oxygen saturation.

Specifically, two lights having discrete frequencies in the range of about 650–670 nm in the red range and about 800–1000 nm in the infrared range are typically passed through the tissue. If blood saturation is constant, variations in absorbance are caused by changes in the amount of blood present in the light path, assumed to be primarily due to arterial blood volume variations corresponding to the arterial pulse. Further, because absorbance of oxyhemoglobin differs for light at the two wavelengths, a ratio of change in absorbance of red to change in absorbance of infrared light can be used to measure oxyhemoglobin percentage.

The signal produced by measuring the light absorption comprises AC and DC components. The AC portion corresponds to varying absorption resulting from pulsatile changes in arterial blood volume while the DC portion is the base optical transmittance that primarily corresponds to tissue, venous blood, and capillary blood absorption. As such, the AC portion of the signal contains a component that is a waveform representative of the patient's blood gas saturation. This component is referred to as a "plethysmographic wave or waveform" (see curve P in FIG. 1).

The ratio of absorbance at the two wavelengths that is attributed to the pulsatile component can be correlated to known saturation values to calibrate the obtained oximetry data. In practice, conventional pulse oximetry methods utilize a ratio of logarithms of the amplitude of the AC signal, i.e., the pulse amplitude, to determine this ratio. The saturation measurements are conventionally determined using the amplitude at maximum and minimum values in the plethysmographic wave to improve the signal to noise ratio.

A difficulty associated with pulse oximetry is that the relative strength of the AC signal as compared to the base optical transmittance has been observed to vary between patients by more than two orders of magnitude. For example, maximal pulse amplitudes range from less than 0.1% to over 10% of measured base optical transmittance among different patients.

Some aspects of the noted pulse amplitude variation are sensor and sensor attachment related. However, the majority of variations originate from the physical extension of the small arterial blood vessels during the pulse pressure wave which is determined by cardiac contractility and arterial vessel wall distensibility. Thus, the relative strength of the pulse amplitude signal is a patient characteristic and, for the purpose of oximetry data collection, is not amenable to being optimized.

As will be discussed in detail below, the ratio of logarithms that corresponds to the ratio of absorbance is non-linearly dependent on the amplitude of the pulse signal. Accordingly, the wide variations in relative pulse amplitude strength between patients can lead to inherent inaccuracies in the determination of blood oxygen saturation. No conventional methods of pulse oximetry have recognized and compensated for the errors in oximetry data attributed to variability in pulse amplitudes.

It is accordingly an object of the present invention to provide a method and apparatus for improving the accuracy of pulse oximetry data.

It is another object of the invention to provide a method and apparatus for compensating for variation in pulse amplitude between patients.

Yet another object of the invention is to provide calibration data relating the ratio of logarithms to oxygen saturation at a plurality of pulse amplitudes.

SUMMARY OF THE INVENTION

In accordance with the above objects and those that will be mentioned and will become apparent below, the invention includes a device for monitoring a physiological characteristic of a patient's blood having first and second radiation emitters that emit light at first and second wavelengths, a radiation detector configured to receive light at the first and second wavelengths after absorbance through the patient's blood and provide first and second intensity signals corresponding to the first and second received wavelengths, and a controller for computing the physiological characteristic of the patient's blood by determining a pulse amplitude associated with the first and second intensity signals and indexing a monitored mathematical combination of the first and second intensity signals to the determined pulse amplitude, wherein the monitored mathematical combination is related to the physiological characteristic and calculated from the first and second intensity signals.

In one embodiment, the device is configured to determine arterial oxygen saturation.

Preferably, the first wavelength is in the range of approximately 650–670 nm. Also preferably, the second wavelength is in the range of 800–1000 nm.

In one embodiment of the invention, the mathematical combination is a ratio of the first and second intensity signals. Preferably, the value is indexed to a stored calibration dataset relating the ratio to oxygen saturation at a specific pulse amplitude. Also preferably, a plurality of stored calibration datasets are provided that relate the ratio to oxygen saturation at a plurality of pulse amplitudes in the range of approximately 0.1% to 10%. In another embodiment, the stored calibration datasets comprise a plurality of datasets at pulse amplitudes in the range of approximately 0.1% to 1%.

According to one aspect of the invention, the controller determines the pulse amplitude from the second intensity signal. Preferably, the controller determines the pulse amplitude in reference to a first amplitude minimum in the second intensity signal. Alternatively, the controller determines the pulse amplitude in reference to a first and a second amplitude minimum in the second intensity signal.

In one embodiment of the invention, the indexing occurs at a plurality of pulse amplitudes in a given pulse. Alternatively, the monitored mathematical combination is calculated from an average of a plurality of pulses.

In a currently preferred embodiment, the monitored mathematical combination is indexed to a maximum determined pulse amplitude.

The invention also comprises a method for processing signals reflecting a physiological characteristic of a patient's blood, comprising the steps of (i) coupling an oximeter sensor arrangement to a tissue region of the patient; (ii) passing first and second lights through the patient's tissue region, wherein the first light is substantially in a red light range and the second light is substantially in an infrared light range; (iii) detecting the first and second lights absorbed by the tissue region and providing a first and second intensity signal corresponding to the absorbed first and second lights; (iv) determining a pulse amplitude associated with the first and second intensity signals; (v) calculating a monitored mathematical combination of the first and second intensity signals, wherein the monitored mathematical combination is related to the physiological characteristic; and (vi) indexing the monitored mathematical combination to the determined pulse amplitude. Preferably, the physiological characteristic determined is arterial oxygen saturation.

In one embodiment of the invention, the monitored mathematical combination is a ratio of the first and second intensity signals.

Preferably, the step of indexing comprises relating the ratio to a stored calibration dataset. In one embodiment of the invention, a plurality of stored calibration datasets corresponding to pulse amplitudes in the range of approximately 0.1% to 10% are used. In another embodiment of the invention, a plurality of stored calibration datasets corresponding to pulse amplitudes in the range of approximately 0.1% to 1% are used.

According to a further aspect of the invention, wherein the second light comprises an infrared wavelength, the pulse amplitude is determined from the second intensity signal. In one embodiment, the pulse amplitude is determined in reference to a first amplitude minimum in the second intensity signal. In another embodiment, the pulse amplitude is determined in reference to a first and a second amplitude minimum in the second intensity signal.

In a further embodiment of the invention, the step of indexing is performed a plurality of times within a given pulse. Alternatively, the step of calculating the monitored mathematical combination comprises determining an average of a plurality of pulses.

In yet another embodiment of the invention, the step of indexing the monitored mathematical combination comprises indexing the value to a maximum determined pulse amplitude.

In accordance with another embodiment, the invention comprises a method for determining a subject's arterial oxygen saturation comprising the steps of i) determining arterial oxygen saturation as a function of a mathematical combination of two optical signals at each of a plurality of specific pulse amplitudes, ii) storing the arterial oxygen saturation functions, iii) obtaining oximetry data from a subject, iv) determining the subject's pulse amplitude, v) monitoring a mathematical combination of two optical signal obtained from the oximetry data, vi) selecting a stored arterial oxygen saturation function having the closest pulse amplitude to the determined pulse amplitude, and vii) determining the subject's arterial oxygen saturation from the monitored mathematical combination and the stored arterial oxygen saturation function having the closest pulse amplitude.

In another embodiment of the invention, the noted method further comprises the step of interpolating the stored arterial oxygen function having the closest amplitude to the determined pulse amplitude to more closely correspond to the measured mathematical combination.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE INVENTION

Before describing the present invention in detail, it is to be understood that this invention is not limited to particularly exemplified materials, methods or structures as such may, of course, vary. Thus, although a number of materials and methods similar or equivalent to those described herein can be used in the practice of the present invention, the preferred materials and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise.

Definitions

The term "signal", as used herein, is meant to mean and include an analog electrical waveform or a digital representation thereof, which is collected from a biological or physiological sensor.

The term "dataset", as used herein, is meant to mean and include data relating a mathematical combination of detected optical signals to saturation at a specific pulse amplitude. For example, each dataset can comprise the calibration relating the ratio of logarithms to arterial oxygen saturation for a given pulse amplitude. Preferably, as described below, a plurality of datasets are used, each at different pulse amplitude, so that a dataset having a pulse amplitude that closely matches a given patient's pulse amplitude can be used.

The terms "patient" and "subject", as used herein, mean and include humans and animals.

As noted above, conventional pulse oximeters fail to compensate for variations in the relative strength of the pulse amplitude signal between patients, which are highly variable. Therefore, while the use of the maximal and minimal pulse amplitudes for a given patient typically represents the best signal to noise ratio, the saturation calculation is performed at a different pulse amplitude depending upon the patient. Since the ratio of logarithm calculations used to determine arterial oxygen saturation exhibit a significant pulse amplitude dependency, prior art pulse oximeters have inaccuracies corresponding to this pulse amplitude dependency. Indeed, any value based upon a mathematical combination of the fundamental oximetry signals is susceptible to pulse amplitude dependency.

The present invention substantially increases the accuracy of conventional pulse oximetry systems, apparatus and techniques. As discussed in detail herein, the method and apparatus for determining a physiological characteristic comprises detecting the intensity of light following tissue absorption at two wavelengths, estimating the pulse amplitude and indexing a calculated physiological characteristic to the estimated pulse amplitude.

By providing a means for indexing the values derived from the oximetry signal to one or more pulse amplitudes, this invention compensates for the inaccuracies associated with the variability of pulse amplitude between patients. Accordingly, pulse amplitudes can be determined accurately and used to provide additional information that substantially improves accuracy of the ratio of logarithms accuracy within the same patient or between different patients. Thus, pulse amplitude indexing links a measured ratio of logarithms obtained from a patient having a specific pulse amplitude to stored calibration data that relates the ratio of logarithms to oxygen saturation at a predetermined pulse amplitude. More accurate oximetry determinations can be made by using calibration data at a pulse amplitude that closely matches the pulse amplitude of the patient. In one embodiment of the invention, pulse amplitude indexing is performed on a pulse average. More preferably, pulse amplitude indexing is performed during every pulse for optimal patient management.

Figure 1:
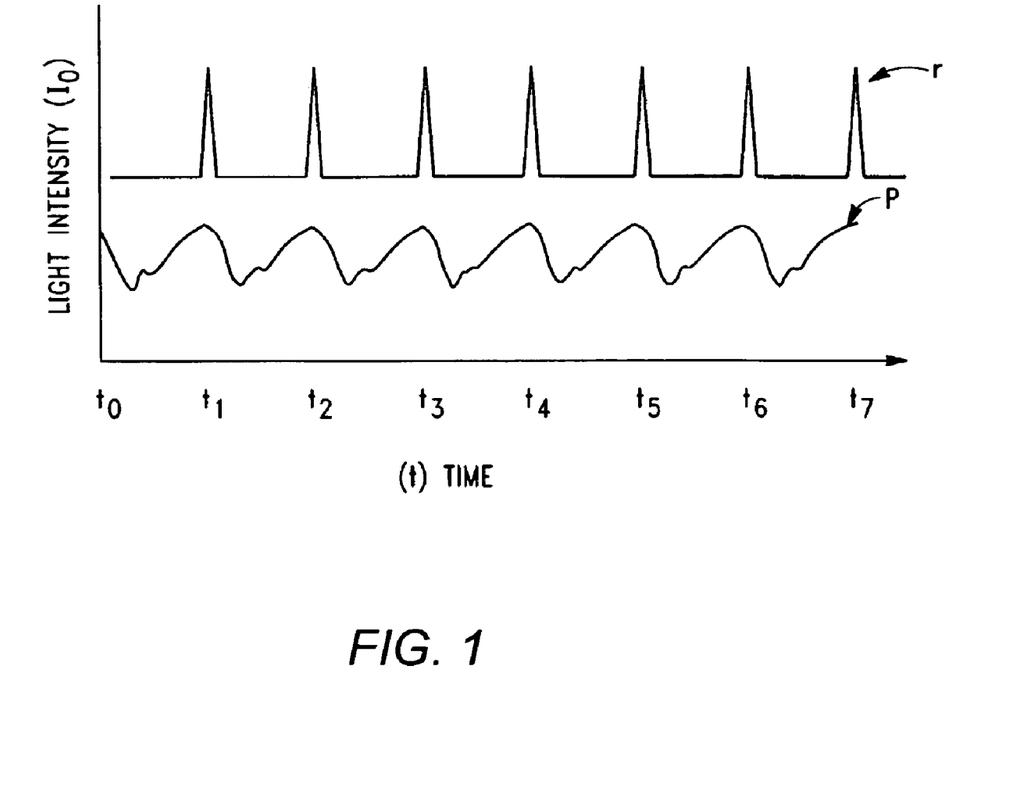
FIG. 1 is a graphical illustration of an r-wave portion of an electrocardiogram waveform and the related plethysmographic waveform.

Referring first to FIG. 1, there is shown a graphical illustration of an "r-wave" portion of an electrocardiogram (ECG) waveform (designated "r") and the related plethysmographic waveform (designated "p"). As will be appreciated by one having ordinary skill in the art, the ECG waveform comprises a complex waveform having several components that correspond to electrical heart activity. The QRS component relates to ventricular heart contraction.

The r-wave portion of the QRS component is typically the steepest wave therein, having the largest amplitude and slope, and may be used for indicating the onset of cardiovascular activity. The arterial blood pulse flows mechanically and its appearance in any part of the body typically follows the R wave of the electrical heart activity by a determinable period of time that remains essentially constant for a given patient. See, e.g., Goodlin et al., Systolic Time Intervals in the Fetus and Neonate, Obstetrics and Gynecology, Vol. 39, No. 2, (February 1972) and U.S. Pat. No. 3,734,086.

Figure 2:
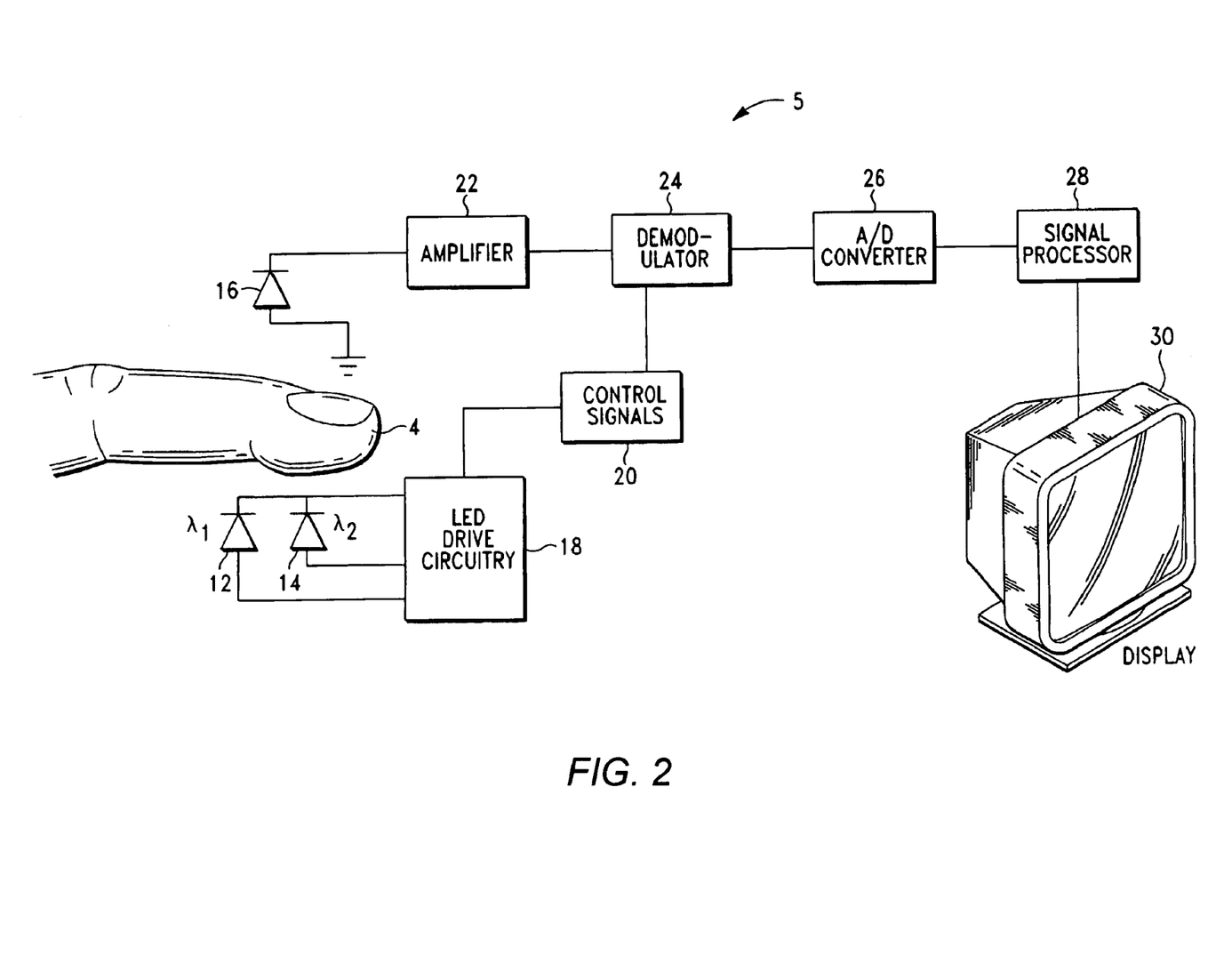
FIG. 2 is a schematic illustration of a pulse oximeter apparatus, according to the invention.

Referring now to FIG. 2, there is shown a schematic illustration of one embodiment of a pulse oximeter apparatus 5 that can be employed within the scope of the invention. As discussed above, conventional pulse oximetry methods and apparatus typically employ two lights; a first light having a discrete wavelength in the range of approximately 650–670 nm in the red range and a second light having a discrete wavelength in the range of approximately 800–1000 nm. For example, a suitable red LED emits light at approximately 660 nm and a suitable infrared LED emits light at approximately 880 nm.

The lights are typically directed through a finger 4 via emitters 12, 14 and detected by a photo detector 16, such as a square photodiode with an area of 49 mm$^2$. Emitters 12 and 14 are driven by drive circuitry 18, which is in turn governed by control signal circuitry 20. Detector 16 is in communication with amplifier 22. In one embodiment, the LEDs are activated at a rate of 8,000 times per second (8 kHz) per cycle, with a cycle comprising red on, quiescent, IR on, quiescent. In the noted embodiment, the total cycle time is 125 microseconds and the LEDs are active for approximately 41.25 microseconds at a time.

The photo detector 16 provides an output signal that is transmitted to an amplifier 22. The amplified signal from amplifier 22 is then transmitted to demodulator 24, which is also synched to control signal circuitry 20. As will be appreciated by one having skill in the art, the output signal from the demodulator 24 would be a time multiplexed signal comprising (i) a background signal, (ii) the red light range signal and (iii) the infrared light range signal.

The demodulator 24, which is employed in most pulse oximeter systems, removes any common mode signals present and splits the time multiplexed signal into two (2) channels, one representing the red voltage (or optical) signal and the other representing the infrared voltage (or optical) signal.

As illustrated in FIG. 2, the signal from the demodulator 24 is transmitted to analog-digital converter (ADC) 26. The desired computations are performed on the output from the converter 26 by signal processor (DSP) 28 and the results transmitted to display 30. In one embodiment, ADC 26 converts the analog signals into 16-bit signed digital signals at a rate of 8 kHz. Further, DSP 28 preferably notch filters the data at 40 Hz to eliminate power line frequency noise limit high frequency noise from other sources. Also preferably, the DSP then parses each data stream by a factor of 4 to give two digital data streams at a rate of 2 kHz.

Further details of the conventional pulse oximeter components, and related functions, are set forth in U.S. Pat. No. 4,934,372, which is incorporated by reference herein.

In one embodiment, the system electronics are configured so that emitters 12 and 14 are driven with a variable gain to produce an AC signal (corresponding to the photoplethysmograph pulse waveform) riding on a larger DC signal. The range of values corresponding to the AC signal represent the pulse amplitude at various points during a pulse wave. The current supplied to the emitters is feedback driven to produce a constant DC signal of approximately 1.25 V, for both the red and infrared signals. The actual DC value is reported continuously. The magnitude of the AC signals is computed relative to the DC signal. The AC component is the signal that is given to the ADC 26 and converted to digital, with the DC signal treated as the "zero point". This creates a factor of the voltage range of the ADC 26 divided by the dynamic (digital) range of the DSP 28. As one having skill in the art will recognize, actual AC voltage level is computed by multiplying the digital AC counts are multiplied by the voltage conversion factor times the DC voltage.

As will be appreciated by those of skill in the art, the noted signals optionally can be subjected to processing steps to improve their quality. In one example, the signals can be processed as described in Co-Pending U.S. patent application Ser. No. 11/270,241, filed Nov. 8, 2005 which is hereby incorporated by reference in its entirety. In the noted application, the red and infrared signals are corrected by applying a residual corresponding to noise that is derived from an average of the red and infrared signals as multiplied by a residual factor subtracted from a difference between the red and infrared signals. However, this step is not intended to be limiting and is not required to practice the invention.

The AC signals can also be processed by any other suitable method, including processes related to obtaining the averages of many single pulses or limiting the evaluation to the maximal amplitude of the each pulse wave signal.

According to the invention, the ratio of logarithms of the amplitude of the red and infrared signals is indexed to the pulse amplitude. By minimizing the pulse amplitude dependence, a more accurate determination of blood oxygen saturation can be provided.

Figures 3, 4:
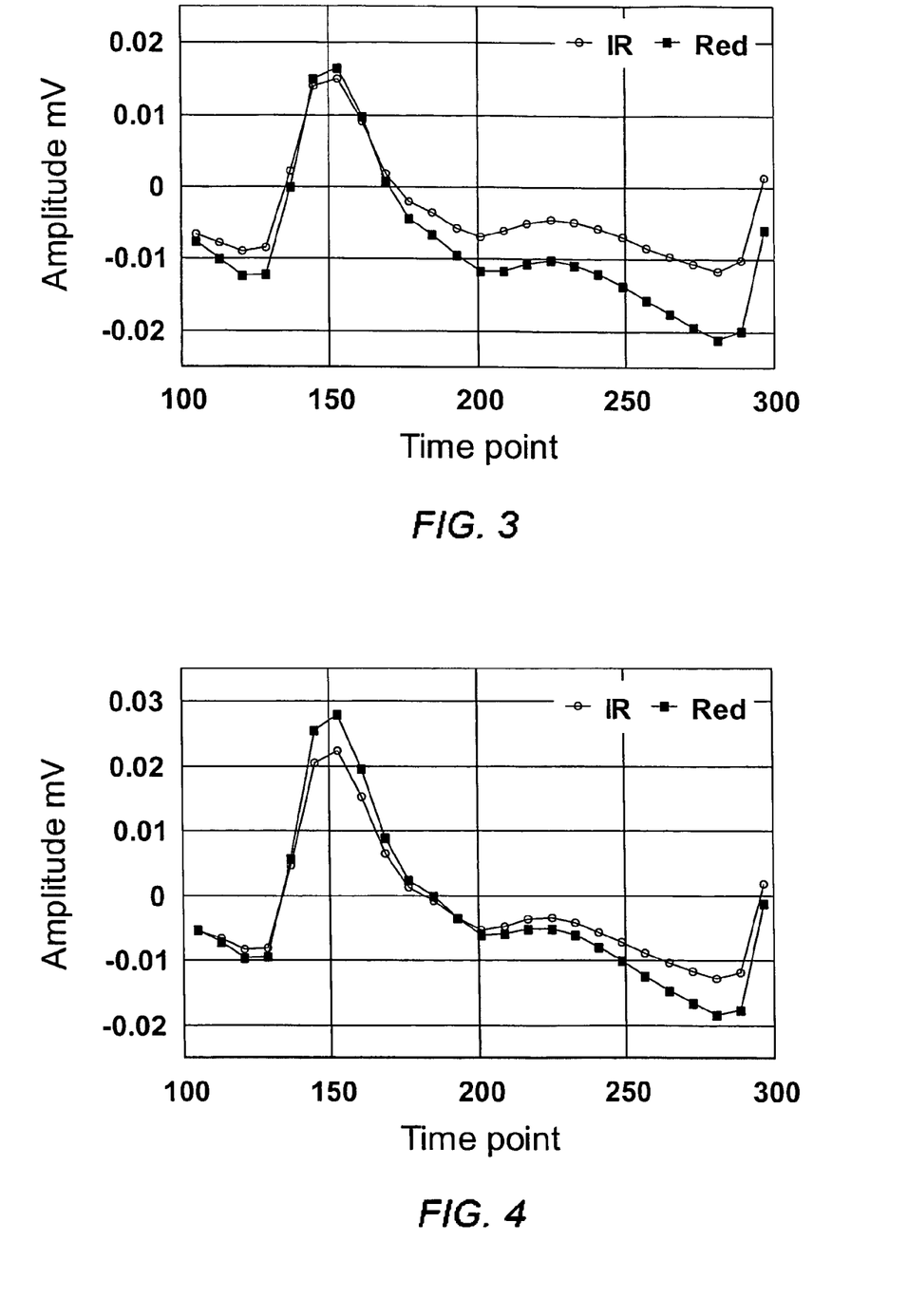
FIGS. 3 and 4 are graphical illustrations of red and infrared optical signals taken from independent sensors.

The specifics of this process are discussed below with respect to exemplary signal data obtained from pulse oximeter 5 using two independent sensors A and B, for example, sensors attached to the index finger of each hand of a subject. FIGS. 3 and 4 show data collected by during a single pulse, from sensors A and B. Both outputs of the sensors are then converted to amplitudes in mV, $A_{IR}$ and $A_{Red}$. The data shown has also been corrected as described in the above-referenced patent application. Preferably, maximal and minimal amplitudes of the data streams are determined using a comparator on a continuous moving average of 50 samples.

In accordance with one embodiment of the invention, pulse amplitudes (PA) are first determined at all time points, including the maximal pulse amplitude, as the difference between the amplitude at any time point and a reference minimum, relative to the DC value. For example, the maximum amplitude shown in FIG. 3 occurs at approximately time point 150. In a preferred embodiment, the reference minimum is the first minimum in the signal, which is shown in FIG. 3 as occurring at approximately time point 125. In other embodiments, a different reference minimum can be established, for example, a minimum derived from the first and second minimums. As shown in FIG. 3, the second minimum occurs at approximately time point 290.

Preferably, the best estimate of pulse amplitude in percent is calculated from the infrared signal because it is less dependent on blood oxygen saturation than the red signal. The infrared amplitudes are then corrected at all time points during a selected pulse wave by applying the following empirically determined linear correction, wherein Sat is the saturation in percent:

$$PA = 100*(PA_{max}/1.25) + ((PA_{max}/1.25)*(-5.58 + (8.17*Sat))/100))$$

The resulting PA values are percentages in the range of approximately 0.1 and 10 for most pulses. As one having skill in the art will appreciate, the factors used in the correction can be adjusted as necessary.

As discussed above, determining the pulse amplitude provides additional information for substantially improving the accuracy oximetry determinations from the monitored ratio of logarithms of the same patient or between different patients. Given the significant pulse amplitude dependency at the same oxygen saturation, the accuracy of the ratio of logarithms, or any other mathematical combination of the fundamental oximetry signals such as the ratio of the red to the infrared signals, or the ratio of red to infrared signals after normalizing for specific DC values, can be improved by indexing it to one or more pulse amplitudes for every pulse.

In practice, pulse amplitude indexing is achieved by applying patient data at different pulse amplitudes from different patients over a wide saturation range to create a calibration dataset relating the ratio of logarithms to saturation for any desired pulse amplitude over the entire expected range of less than 0.1% to over 10%. In one embodiment, a calibration data set having a resolution of 0.1% is used.

As can be appreciated, the accuracy of determinations can be improved by increasing the number of data sets stored in the oximeter to provide greater resolution for indexing.

As discussed above, the ratio of logarithms is a useful parameter for conversion to saturation and calibration of oximeters. The simplicity is due in part by the engineering design of driving the LED intensity until a given baseline optical transmittance (DC) is reached. AC/DC is the ratio of transmittances but since the DC signal is configured to be constant, the ratio of the logarithms is equivalent to the ratio of absorbances.

Thus, the ratio of logarithms is the principal measurement parameter that relates to reference saturation percent for calibrating pulse oximeters. It is calculated from the amplitudes $A_{IR}$ and $A_{Red}$. The first step is to bring the amplitudes of the red and infrared signals $A_{RedMin}$ and $A_{IRMin}$, which represent the equivalent of optical transmittance to zero. This operation can be performed at either the first minimum or at the average of the first and the second minimum. The ratio R is then calculated as the absolute logarithm of the zeroed red amplitude over the absolute logarithm of the zeroed infrared amplitudes:

$$R = |(\log(A_{Red} - A_{RedMin}))|/|(\log A_{IR} - A_{IRMin}))|$$

The resulting ratio of logarithms of the absorbances is analyzed as a function of pulse amplitude during an average or, more preferably, during a single pulse, to derive a pulse amplitude indexed ratio of logarithms which can be calibrated to CO-oximetry reference data in a conventional manner.

Figure 5:
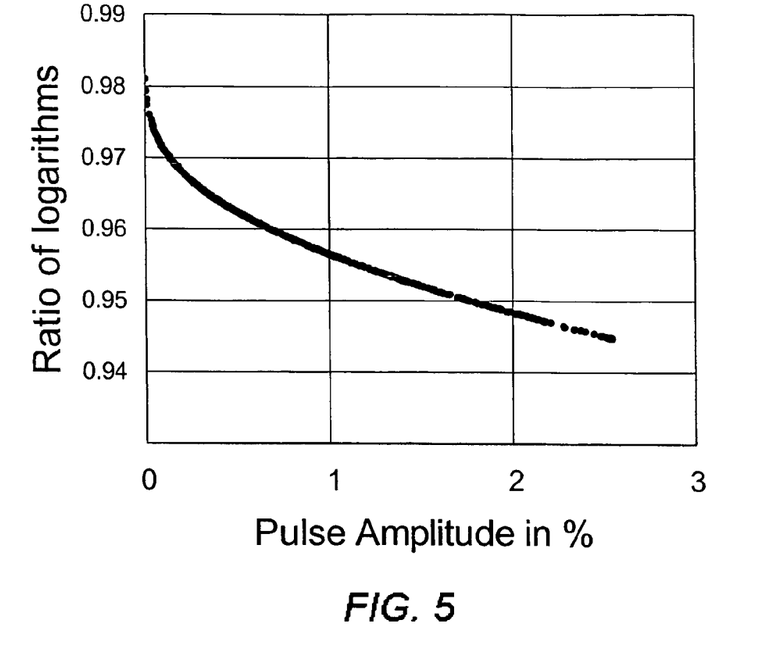
FIGS. 5 and 6 are graphical illustrations of pulse amplitude as a function of ratio of logarithms taken from independent sensors for a single pulse at relatively low oxygen saturation, according to the invention.
Figure 6:
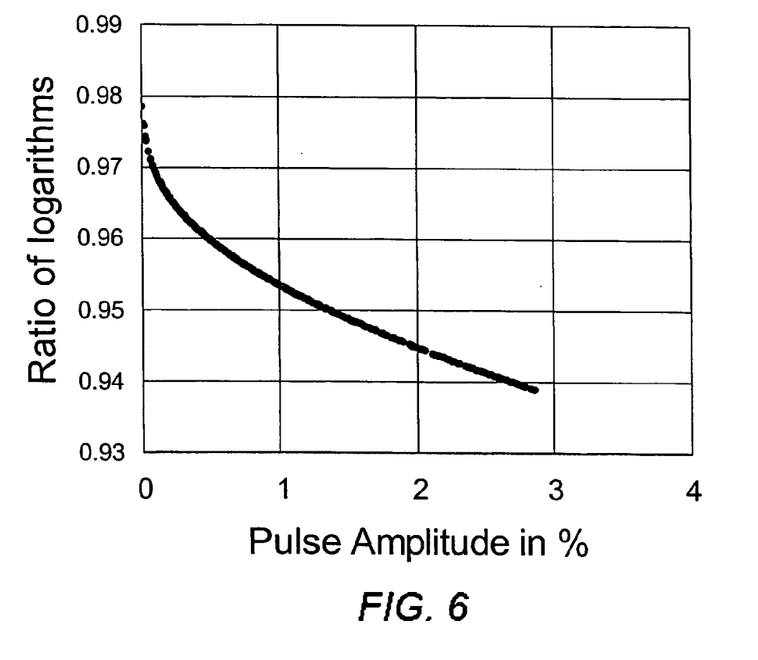

Exemplary data indicating relationship between pulse amplitude and the ratio of logarithms is shown in FIGS. 5–8. FIGS. 5 and 6 relate the calculated PA to the ratio of logarithms in a single selected pulse at a known saturation from two independent sensors. The data demonstrate that PA substantially influences the ratio of logarithms as evidenced by the changing ratio values at different pulse amplitudes, despite the constant saturation.

Figure 7:
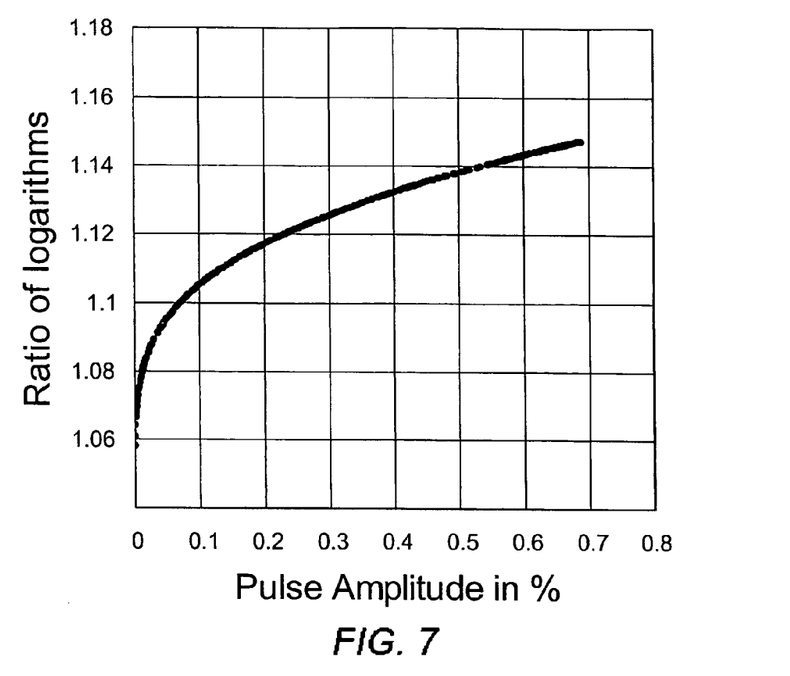
FIGS. 7 and 8 are graphical illustrations of pulse amplitude as a function of the ratio of logarithms for a single pulse obtained from different patients at relatively high oxygen saturation, according to the invention.
Figure 8:
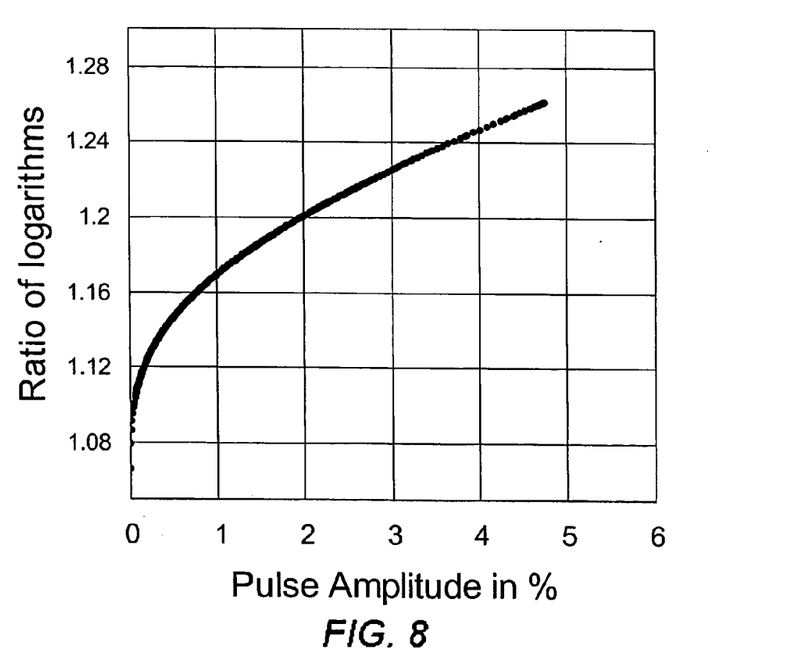

FIGS. 7 and 8 compare the ratio of logarithms between two patients exhibiting varying ranges of pulse amplitude at similar saturations. The data represented in FIG. 7 was collected from a patient that exhibited a relatively weak pulse amplitude signal as compared to the baseline optical transmittance, less than 0.1%. In contrast, the data in FIG. 8 was collected from a patient that exhibited a relatively strong pulse amplitude signal, greater than 4%. By comparing the results shown in FIGS. 7 and 8, it is clear that the higher pulse amplitudes correlate with higher ratios, despite substantially equivalent saturations.

It has been determined that there is a positive correlation between pulse amplitude and the ratio of logarithms is positive at saturations greater than about 84%, such as shown in FIGS. 7 and 8, and a negative correlation at lower saturations, such as shown in FIGS. 5 and 6. The effects increase as saturation deviates from 84%. Clearly, failure to accommodate the impact of pulse amplitude on the ratio of logarithms can represent a significant inaccuracy.

According to the invention, data such as that illustrated in FIGS. 5–8 are collected from individual patients at different saturations and different pulse amplitudes. Using this information, the monitored ratio of logarithms from a patient is indexed to the calculated PA at each timepoint in the plethysmograph wave to compensate for the pulse amplitude dependency. In this manner, substantially more accurate pulse oximetry data can be obtained.

In one embodiment of the invention, the calculations described above are used to provide a method for determining arterial oxygen saturation with pulse amplitude indexing. Specifically, arterial oxygen saturation as a function of the ratio of logarithms is determined at each of a plurality of specific pulse amplitudes over a desired range and stored. Oximetry data is then obtained from a subject and the subject's pulse amplitude is determined. A monitored ratio of logarithms for the subject is calculated from the obtained data. A stored arterial oxygen saturation function at a pulse amplitude that closely matches the subject's pulse amplitude is selected. Then, the monitored ratio of logarithms is used with the selected arterial oxygen saturation function to determine the arterial oxygen saturation of the subject. Preferably, the stored arterial oxygen saturation function having the closest pulse amplitude can be interpolated to more closely match the monitored ratio of logarithms.

As discussed above, data from a plurality of subjects subjected to desaturation by inhalation of hypoxic gas mixtures is collected. Arterial oxygen saturation as a function of the ratio of logarithms is tabulated at a range of pulse amplitudes to create a dataset array. Accordingly, each row of the array contains the expected ratio of logarithms for a given pulse amplitude for a known saturation.

The stored saturation data then can be used with pulse oximetry monitoring to determine arterial oxygen saturation. For example, the monitored IR signal is corrected as described above using an empirically derived formula. As noted, the pulse amplitude of a given pulse can be computed by determining the ratio of voltages of the AC component of the infrared signal to the DC component:

voltage ratio=(voltage IR)/(voltage DC)

A saturation factor can be calculated as follows:
saturation factor=−5.58+(8.17*saturation), with saturation expressed as a fraction The voltage ratio and saturation factor then can be combined to calculate the pulse amplitude:

PA=((saturation factor*voltage ratio/100)+voltage ratio)*100

Thus, the calculated pulse amplitude and the ratio of logarithms as monitored can be used to make a best fit approximation of saturation from the stored arterial saturation data using standard techniques, such as a least-squares estimate. Preferably, the array datasets can be interpolated to provide precise calculations of saturation for any pulse amplitude and any ratio of logarithms.

In other embodiments, an alternate mathematical combination of the red and infrared signals can be used in place of the ratio of logarithms.

EXAMPLES

The following examples are given to enable those skilled in the art to more clearly understand and practice the present invention. They should not be considered as limiting the scope of the invention, but merely as being illustrated as representative thereof.

Example 1

A study comparing oximetry determinations using the pulse amplitude indexed ratio of logarithms as described above to non-indexed values was performed with 8 adult volunteers. For the study, a catheter was placed into a radial artery of each subject. A Nellcor N-200 pulse oximeter was used as a reference device, and also for clinically monitoring the subject. Each subject was given varying inspired concentrations of oxygen in order to produce arterial hemoglobin oxygen saturations in the approximate range of 70–100%.

Experimental oximetry readings were obtained from two independent sensors at separate locations on each patient, such as on the fingers of opposing hands, for confirmation of results, duplication of data, and extraction of additional physiological information. The data from each sensor was processed independently.

Blood samples were drawn from the arterial catheter simultaneously with readings of oxygen saturation, and immediately analyzed. Data were collected of both the waveform being analyzed, as well as computed intermediate steps. The arterial blood sample was analyzed on two separate blood-gas analyzers by Radiometer. The functional saturation of hemoglobin was computed as oxyhemoglobin/(total hemoglobin). That is, all non-oxyhemoglobin species were included in total hemoglobin. At all saturations and for all human study subjects, the reference values for the algorithmically computed values were the average readings from two CO-oximeters.

Figure 9:
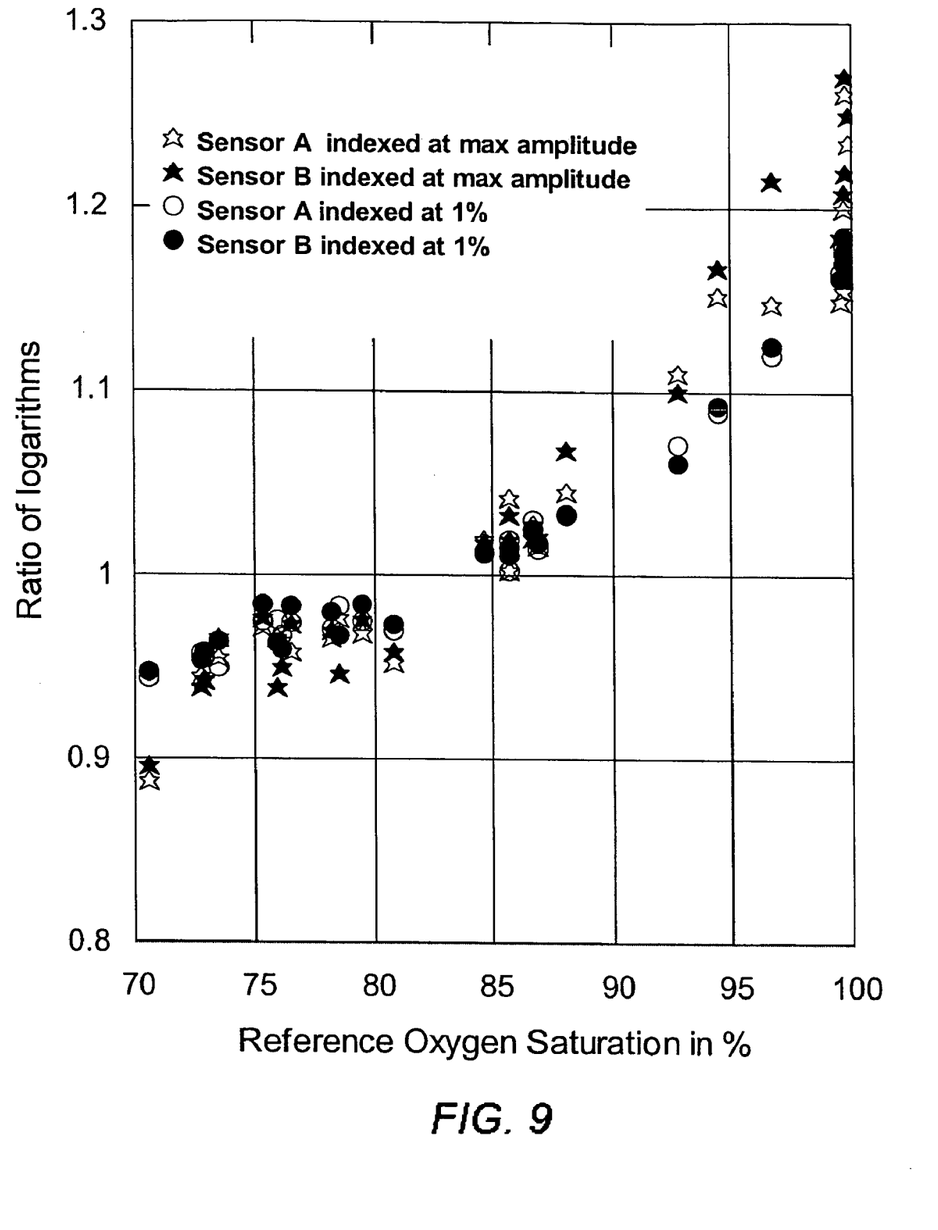
FIG. 9 is a graphical illustration comparing pulse amplitude indexed and conventional ratio of logarithms as a function of oxygen saturation, according to the invention.

The results of the noted study are shown in FIG. 9. The use of two independent sensors demonstrates that greater precision was obtained when the ratio of logarithms is indexed to pulse amplitude, rather than simply being determined at the maximal amplitude. These results indicate that an increase in precision of up to five-fold is possible by pulse amplitude indexing. As can be seen, the improvements provided by amplitude indexing are largest at higher and lower saturations and smallest around 84%.

In this example, the ratios of logarithms were indexed to a pulse amplitude of 1%. However, as one having skill in the art can appreciate, any amplitude can be chosen for which reference data are available. In a preferred embodiment, the highest pulse amplitude available for each pulse is employed in order to maximize the signal to noise ratio. At high amplitudes, the calibration curve also has a steeper slope, which results in improved resolution of the measured saturation parameter.

It is also preferable to have indexing data for as many saturations and pulse amplitudes at a resolution of less than 1% pulse amplitude, such as 0.1%, as practical.

By employing the above methods, the most precise data points are selected and indexed to eliminate deviations caused by pulse amplitude to achieve and maintain the highest possible oximetry accuracy.

In additional embodiments, the principles represented by the present invention can also be applied to a wide variety of other biological and physiological determinations. For example, U.S. Pat. Nos. 6,480,729, 6,537,225, 6,594,511, 6,719,705, 6,819,950, and 6,921,367 and U.S. application Ser. No. 10/912,721, filed 4 Aug. 2004, all of which are incorporated in their entirety by reference, each relate to the acquisition of signals for determining physiological characteristics and can be practiced with the methods and apparatus of the present invention.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A device for the monitoring of a physiological characteristic of a patient's blood, comprising:
    a first radiation emitter that emits light at a first wavelength;
    a second radiation emitter that emits light at a second wavelength;
    a radiation detector configured to receive light at said first and second wavelengths after absorbance through said patient's blood and provide a first intensity signal and a second intensity signal corresponding to said first and second received wavelengths; and
    a controller for computing said physiological characteristic of said patient's blood by determining a pulse amplitude associated with said first and second intensity signals and indexing a monitored mathematical combination of said first and second intensity signals to said determined pulse amplitude, wherein said monitored mathematical combination is related to said physiological characteristic and calculated from said first and second intensity signals.

2. The device of claim 1, wherein said physiological characteristic is arterial oxygen saturation.

3. The device of claim 2, wherein said first wavelength is in the range of approximately 650–670 nm.

4. The device of claim 2, wherein said second wavelength is in the range of 800–1000 nm.

5. The device of claim 1, wherein said monitored mathematical combination is a ratio of said first and second intensity signals.

6. The device of claim 5, wherein said controller further comprises a stored calibration dataset relating said ratio to oxygen saturation at a specific pulse amplitude.

7. The device of claim 6, wherein said controller further comprises a plurality of stored calibration datasets that relate said ratio to oxygen saturations at a plurality of pulse amplitudes in the range of approximately 0.1% to 10%.

8. The device of claim 7, wherein said stored calibration datasets comprise a plurality of datasets at pulse amplitudes in the range of approximately 0.1% to 1%.

9. The device of claim 4, wherein said controller determines said pulse amplitude from said second intensity signal.

10. The device of claim 9, wherein said controller determines said pulse amplitude in reference to a first amplitude minimum in said second intensity signal.

11. The device of claim 9, wherein said controller determines said pulse amplitude in reference to a first and a second amplitude minimum in said second intensity signal.

12. The device of claim 1, wherein said indexing occurs at a plurality of pulse amplitudes in a given pulse.

13. The device of claim 1, wherein said monitored mathematical combination is calculated from an average of a plurality of pulses.

14. The device of claim 1, wherein said monitored mathematical combination is indexed to a maximum determined pulse amplitude.

15. A method for processing signals reflecting a physiological characteristic of a patient's blood, comprising the steps of:
    coupling an oximeter sensor arrangement to a tissue region of said patient;
    passing first and second lights through said patient's tissue region, wherein said first light is substantially in a red light range and said second light is substantially in an infrared light range;
    determining a pulse amplitude associated with said first and second intensity signals;
    calculating a monitored mathematical combination from said first and second intensity signals, wherein said monitored mathematical combination is related to said physiological characteristic; and
    indexing said monitored mathematical combination to said determined pulse amplitude.

16. The method of claim 15, wherein said physiological characteristic is arterial oxygen saturation.

17. The method of claim 15, wherein said monitored mathematical combination is a ratio of said first and second intensity signals.

18. The method of claim 17, wherein the step of indexing comprises relating said ratio to a stored calibration dataset.

19. The method of claim 17, wherein the step of indexing comprises relating said ratio to a plurality of stored calibration datasets corresponding to pulse amplitudes in the range of approximately 0.1% to 10%.

20. The method of claim 19, wherein the step of indexing comprises relating said ratio to a plurality of stored calibration datasets corresponding to pulse amplitudes in the range of approximately 0.1% to 1%.

21. The method of claim 15, wherein said second light comprises an infrared wavelength and wherein said pulse amplitude is determined from said second intensity signal.

22. The method of claim 21, wherein said pulse amplitude is determined in reference to a first amplitude minimum in said second intensity signal.

23. The method of claim 21, wherein said pulse amplitude is determined in reference to a first and a second amplitude minimum in said second intensity signal.

24. The method of claim 15, wherein the step of indexing is performed a plurality of times within a given pulse.

25. The method of claim 15, wherein the step of calculating said monitored mathematical combination comprises determining an average of a plurality of pulses.

26. The method of claim 15, wherein the step of indexing said monitored mathematical combination comprises indexing said value to a maximum determined pulse amplitude.

27. A method for determining a subject's arterial oxygen saturation comprising the steps of:
    determining arterial oxygen saturation as a function of a mathematical combination of two optical signals at each of a plurality of specific pulse amplitudes;
    storing said arterial oxygen saturation functions;
    obtaining oximetry data from a subject;
    determining said subject's pulse amplitude;
    monitoring a mathematical combination of two optical signals obtained from said oximetry data;
    selecting a stored arterial oxygen saturation function having the closest pulse amplitude to said determined pulse amplitude; and determining said subject's arterial oxygen saturation from said monitored mathematical combination and said stored arterial oxygen saturation function having the closest pulse amplitude.

28. The method of claim 27, further comprising the step of interpolating said stored arterial oxygen function having the closest amplitude to said determined pulse amplitude to more closely correspond to said measured mathematical combination.

* * * * *